(12) United States Patent
Basheer et al.

(10) Patent No.: US 9,128,106 B2
(45) Date of Patent: Sep. 8, 2015

(54) DISPERSIVE LIQUID-LIQUID MICROEXTRACTION METHOD OF DETECTING N-NITROSOAMINES

(71) Applicants: KING FAHD UNIVERSITY OF PETROLEUM AND MINERALS, Dhahran (SA); KING ABDULAZIZ CITY FOR SCIENCE AND TECHNOLOGY, Riyadh (SA)

(72) Inventors: Chanbasha Basheer, Karimangalam (IN); Mousa Yasir Mousa Amayreh, Dhahran (SA)

(73) Assignees: KING FAHD UNIVERSITY OF PETROLEUM AND MINERALS, Dhahran (SA); KING ABDULAZIZ CITY FOR SCIENCE AND TECHNOLOGY, Riyadh (SA)

( * ) Notice: Subject to any disclaimer, the term of this patent is extended or adjusted under 35 U.S.C. 154(b) by 0 days.

(21) Appl. No.: 14/072,507

(22) Filed: Nov. 5, 2013

(65) Prior Publication Data

US 2015/0121993 A1    May 7, 2015

(51) Int. Cl.
*G01N 30/72* (2006.01)

(52) U.S. Cl.
CPC ............ *G01N 30/72* (2013.01); *G01N 30/7206* (2013.01)

(58) Field of Classification Search
CPC .................................................. G01N 30/7206
See application file for complete search history.

(56) References Cited

U.S. PATENT DOCUMENTS

| 4,336,158 A | 6/1982 | Frank et al. |
| 5,094,815 A | 3/1992 | Conboy et al. |
| 7,709,264 B2 | 5/2010 | Deevi et al. |

OTHER PUBLICATIONS

Campillo, Natalia et al., "Determination of Volatile Nitrosamines in Meat Products by Microwave-Assisted Extraction and Dispersive Liquid-Liquid Microextraction Coupled to Gas Chromatography-Mass Spectrometry," Journal of Chromatography A, 1218(14), 1815-1821, 2011.
Ojeda, Catalina Bosch et al., "Separation and Preconcentration by Dispersive Liquid-Liquid Microextraction Procedure: Recent Applications," Chromatographia, 74(9-10), 651-679, 2011.

*Primary Examiner* — Laura Martin
*Assistant Examiner* — Alex Devito
(74) *Attorney, Agent, or Firm* — Richard C Litman

(57) ABSTRACT

The dispersive liquid-liquid microextraction (DLLME) method of detecting N-nitrosoamines (NAs) is a DLLME performed with a xylene extraction solvent and a methanol disperser solvent. The microextraction is preferably performed by a programmable array logic (PAL) auto-sampler. Determination and measurement of concentration of the NAs in the water sample being found by a gas chromatograph coupled with a mass spectrometer (GC-MS).

7 Claims, 1 Drawing Sheet

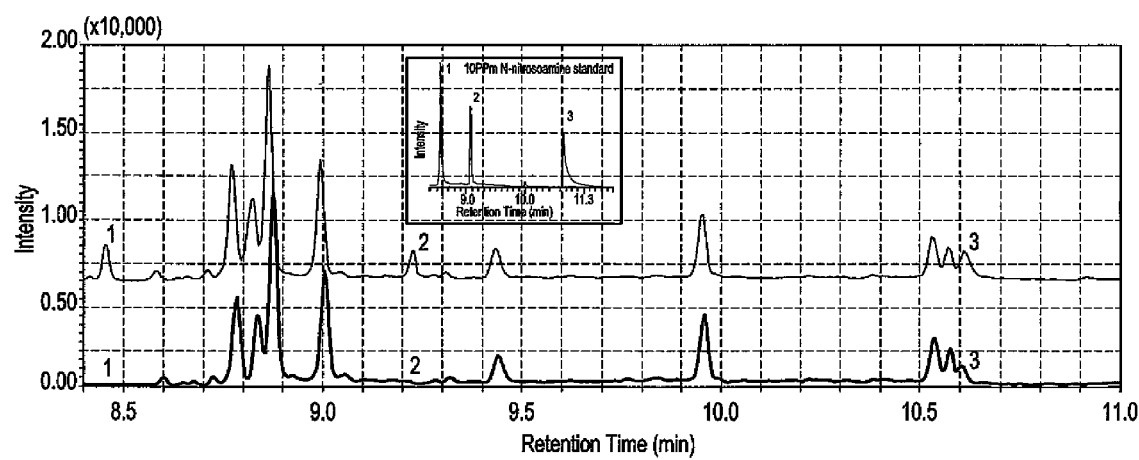

DISPERSIVE LIQUID-LIQUID MICROEXTRACTION METHOD OF DETECTING N-NITROSOAMINES

BACKGROUND OF THE INVENTION

1. Field of the Invention

The present invention relates to separation techniques, and particularly to a dispersive liquid-liquid micro extraction (DLLME) method to detect N-nitrosoamines in aqueous solution.

2. Description of the Related Art

N-nitrosoamines (NAs) are produced by the reaction of amines or their derivatives with nitrosating agents, such as nitrous acid, nitrites, or nitrogen oxides. N-nitrosoamines are compounds that are relatively stable and difficult to break down, once formed. NAs have been in the environment, including drinking water, primarily due to the use of ozone in disinfection processes, as well as a variety of other industrial applications, such as food and cosmetics processing, dye and rubber manufacturing, leather tanning and metal casting. NAs have been found in industrial wastewater and in the effluent of sewage treatment plants. NAs are known to have toxic action in the liver, kidneys and lungs of humans. About 90% of NAs are classified as potent human carcinogens, as well as being teratogenic. There are at least four known sources of NAs in water: direct industrial or human-derived contamination; microbial action; disinfection by-product formation; and natural degradation of precursors.

Due to the polarity of NAs, they are typically soluble in water. NAs discovered in drinking water include N-nitrosomorpholine, N-nitrosopyrrolidine, N-nitrosopiperidine and N-nitrosodiphenylamine. The analysis of N-nitroso-di-n-propylamine (NDPA), N-nitrosopiperidine (NPIP) and N-nitroso-di-n-butylamine (NDBA) in water is of particular interest, as these substances have been included in the carcinogenic compounds category B2 included in the Unregulated Contaminant Monitoring Rule 2 of the United States Environmental Protection Agency. Additionally, NAs are known to be rodent carcinogens, and most are considered as probable human carcinogens by the International Agency for Research on Cancer.

Detection of NAs in water typically involves the use of solid phase microextraction (SPME) or liquid-liquid microextraction (LLME) for separation of the compound, followed by ultimate detection and determination performed by gas chromatography (GC) with a variety of detectors, such as a thermal energy analyzer (GC-TEA), nitrogen chemiluminescence detector (NCD), or nitrogen-phosphorus detector (NPD). Mass spectrometry (MS) is often coupled with GC, achieving high sensitivity as well as excellent identification of the analytes. Tandem mass spectrometry (GC-MS/MS) and high resolution mass spectrometry (GC/HRMS) are also often coupled with GC. Liquid chromatography (LC) has also been applied to the determination of NAs in water, using tandem mass spectrometry (LC-MS/MS). However, LC-MS/MS shows relatively low sensitivity for some nitrosamines. SPME is a solvent-free process based on the pre-concentration of analytes from aqueous samples or the headspace of the samples. SPME, however, is a complex and expensive process, primarily due to its use of specialized, fragile fibers with limited lifetimes. Although less expensive, LLME is not seen as an efficient replacement for SPME, as it is a complex, multi-step process that requires a great deal of time to perform.

Dispersive liquid-liquid microextraction (DLLME), however, is a relatively fast extraction technique based on the use of a ternary component solvent system applied to the pre-concentration of both organic and inorganic compounds from aqueous samples. In this technique, a few microliters of a mixture of two solvents (the extractant solvent and the disperser solvent) are quickly injected into the sample. The extractant solvent is immiscible with water, while the disperser solvent is soluble in both water and the extractant solvent. The disperser solvent enables the extractant solvent to disperse and partition into fine droplets uniformly dispersed in the water-disperser solvent matrix, presenting virtually infinite surface area for extraction of the analyte from the aqueous phase into the extraction solvent, which therefore proceeds very quickly, often. This quickly produces a cloudy suspension of fine droplets, which can be centrifuged or simply left to settle in order to separate the extractant solvent (now containing the analyte) from the water-disperser solvent phase. The analyte may then be analyzed by GC or similar methods. It would obviously be desirable to apply the DLLME technique to the determination of NAs, including N-nitroso-di-n-propylamine (NDPA), N-nitroso-di-n-butylamine (NDBA) and N-nitrosopiperidine (NPIP), in aqueous solution.

Thus, a dispersive liquid-liquid microextraction method of detecting N-nitrosoamines solving the aforementioned problems is desired.

SUMMARY OF THE INVENTION

The dispersive liquid-liquid microextraction (DLLME) method of detecting N-nitrosoamines (NAs) is a DLLME performed with a xylene extraction solvent and a methanol disperser solvent. The microextraction is preferably performed by a programmable array logic (PAL) auto-sampler. Determination and measurement of concentration of the NAs in the water sample being found by a gas chromatograph coupled with a mass spectrometer (GC-MS).

These and other features of the present invention will become readily apparent upon further review of the following specification and drawings.

BRIEF DESCRIPTION OF THE DRAWINGS

The sole drawing FIGURE shows total ion chromatograms produced by the dispersive liquid-liquid microextraction method of detecting N-nitrosoamines according to the present invention, applied to a fresh groundwater sample (the lower trace) and a sample of fresh groundwater spiked with N-nitrosoamines (2 µg/L) (the upper trace).

DETAILED DESCRIPTION OF THE PREFERRED EMBODIMENTS

The dispersive liquid-liquid microextraction (DLLME) method of detecting N-nitrosoamines (NAs) is a DLLME performed with a xylene extraction solvent and a methanol disperser solvent. The microextraction is preferably performed by a programmable array logic (PAL) auto-sampler. Determination and measurement of concentration of the NAs in the water sample being found by a gas chromatograph coupled with a mass spectrometer (GC-MS).

In order to test the efficacy of the present dispersive liquid-liquid microextraction method of detecting N-nitrosoamines, test samples were prepared as follows. About 2.095 g of sodium chloride was added to 10 mL of a water sample (pH adjusted to 10.46), and 1000 µL of a xylene extraction solvent was added manually. The samples were prepared in glass vials, which were then placed in an auto-sampler tray. About 33.57 μL of a methanol disperser solvent and 5 μL of 200 mg/L of NAs were added to the sample vials automatically by an auto-sampler to form 90 μg/L NA concentrations for the optimization study. Three different types of NAs were used: N-nitroso-di-n-propylamine (NDPA), N-nitroso-di-n-butylamine (NDBA) and N-nitrosopiperidine (NPIP). The vials were transported automatically to an agitator and agitated at an agitation speed of 706.15 RPM with an extraction time of 25.77 minutes. Agitation produced a cloudy solution, and the glass vials were transported back to the auto-sampler tray, where they were held for one minute. A programmable array logic (PAL) auto-sampler removed 1 μL of the formed upper organic phase in a 10 μL glass syringe, and this organic phase (i.e., the analyte) was injected directly into a gas chromatograph coupled with a mass spectrometer (GC-MS) for analysis.

For purposes of the analysis, an enrichment factor EF was defined as the ratio between the analyte concentration in the extraction phase $C_{ext}$ and the initial concentration of the analyte $C_0$ in the standard sample, or $EF=C_{ext}/C_0$. $C_{ext}$ was obtained from a calibration graph prepared by direct injection of a phthalic acid esters (PAEs) standard solution into the extraction solvent.

Response Surface Methodology (RSM), a multi-variate statistical modeling technique, was used to evaluate the effects of the independent variables and their interactions on the response, and also to optimize the procedure for extraction and analysis of NAs. RSM involves designing an experiment according to factorial design, thus enabling the development of second-order polynomial models and response surfaces.

Using RSM, the effect of five different parameters were investigated to understand the effects of the parameters and their interactions on the DLLME extraction enrichment factor (EF) and low limits of detection (LODs) of the three NAs (NDBA, NDPA and NPIP), and also to optimize the EFs. These factors included (A) extraction time; (B) volume of dispersive solvent; (C) pH; (D) salt addition; and (E) agitation speed. Box-Behnken design (BBD) was used for developing second-order quadratic models with the aid of a computerized statistical software package. As the BBD experimental design is an orthogonal design, factor levels were evenly spaced and coded for low, medium (central point) and high levels as −1, 0 and +1, respectively, as shown in Table 1, below, and the equation:

$$x_i = \frac{X_i - (X_{high} - X_{low})/2}{(X_{high} - X_{low})/2},$$

where $x_i$ is the coded value and $X_i$ is the original value. A total of forty-one experimental runs were used for implementing the BBD. Replicated center points were introduced to enable evaluation of experimental error and the reproducibility of the data. The experimental run sequences were randomized in order to eliminate the effects of the uncontrolled factors to ensure data quality.

TABLE 1

Actual and Coded Values of five variables in Design Expert

| Variable | Component | Unit | coded and actual level | | |
|---|---|---|---|---|---|
| | | | −1 | 0 | +1 |
| A | Extraction time | min | 10 | 20 | 30 |
| B | Dispersive volume | μL | 15 | 30 | 45 |
| C | PH | — | 4 | 8 | 12 |
| D | Salt addition | % (g/ml) | 0 | 15 | 30 |
| E | Agitation speed | RPM | 250 | 500 | 750 |

The primary experimental parameter of DLLME is the selection of the extraction and dispersive solvents. There are specific criteria for choosing the best extraction solvent, including (i) higher/lower density than water, (ii) the solubility in water is low, (iii) the capability for extraction of analytes from the aqueous phase is high, (iv) the dispersive solvent should be easily dispersed through the dispersive step, and (v) good chromatography behavior. With regard to the disperser solvent, it should further be miscible in both the extraction solvent and the aqueous sample. Tests were performed to find the most suitable extraction and dispersive solvents, specifically examining hexane, isooctane, n-pentane, toluene, and xylene as extraction solvents, and testing methanol, acetonitrile and acetone as disperser solvents. The results of the optimization experiments revealed that xylene as the extraction solvent and methanol as the dispersive solvent provided the best overall performance in the DLLME process.

The values of 41 different combinations of DLLME extraction conditions, based on the following independent variables, along with the corresponding calculated EFs of the extracted NAs, are shown below in Table 2: (A) extraction time; (B) volume of dispersive solvent; (C) pH; (D) salt addition; and (E) agitation speed.

TABLE 2

Experimental Combination Conditions for Determination of Optimization Values for All Variables

| | Independent Variable | | | | | Average of enrichment factor (n = 4) | | | |
|---|---|---|---|---|---|---|---|---|---|
| Exp # | A (min) | B (μL) | C | D (%) | E (rpm) | NDPA | NPIP | NDBA | Total nitrosoamine |
| 1 | 30 | 45 | 8 | 15 | 500 | 50.80 | 25.07 | 40.42 | 116.29 |
| 2 | 30 | 30 | 12 | 15 | 500 | 42.78 | 22.22 | 43.91 | 108.9 |
| 3 | 20 | 30 | 8 | 0 | 750 | 41.20 | 16.46 | 41.74 | 99.4 |
| 4 | 20 | 45 | 8 | 30 | 500 | 32.52 | 16.09 | 19.92 | 68.53 |
| 5 | 10 | 30 | 4 | 15 | 500 | 28.12 | 17.57 | 23.70 | 69.4 |
| 6 | 10 | 30 | 8 | 0 | 500 | 34.98 | 15.56 | 35.98 | 86.51 |
| 7 | 20 | 30 | 8 | 0 | 250 | 53.16 | 13.62 | 31.30 | 98.09 |

TABLE 2-continued

Experimental Combination Conditions for Determination of Optimization Values for All Variables

| Exp # | A (min) | B (μL) | C | D (%) | E (rpm) | NDPA | NPIP | NDBA | Total nitrosoamine |
|---|---|---|---|---|---|---|---|---|---|
| 8 | 30 | 30 | 8 | 30 | 500 | 36.29 | 21.38 | 37.44 | 95.11 |
| 9 | 20 | 15 | 8 | 0 | 500 | 36.48 | 15.48 | 36.12 | 88.08 |
| 10 | 30 | 15 | 8 | 15 | 500 | 28.90 | 10.78 | 19.11 | 58.8 |
| 11 | 10 | 30 | 8 | 15 | 250 | 23.14 | 10.72 | 14.13 | 47.99 |
| 12 | 30 | 30 | 8 | 15 | 750 | 44.50 | 23.46 | 52.47 | 120.43 |
| 13 | 20 | 30 | 4 | 15 | 750 | 37.10 | 21.65 | 34.42 | 93.17 |
| 14 | 20 | 45 | 8 | 15 | 250 | 22.79 | 19.09 | 9.20 | 51.09 |
| 15 | 20 | 30 | 4 | 15 | 250 | 25.04 | 18.32 | 14.03 | 57.39 |
| 16 | 10 | 45 | 8 | 15 | 500 | 35.67 | 17.60 | 23.36 | 76.62 |
| 17 | 20 | 15 | 8 | 15 | 250 | 27.75 | 17.32 | 17.07 | 62.14 |
| 18 | 20 | 30 | 8 | 15 | 500 | 33.96 | 13.94 | 29.02 | 76.91 |
| 19 | 10 | 30 | 8 | 30 | 500 | 27.52 | 17.84 | 18.23 | 63.59 |
| 20 | 20 | 30 | 12 | 15 | 250 | 25.47 | 15.79 | 14.44 | 55.7 |
| 21 | 20 | 45 | 8 | 15 | 750 | 36.66 | 18.66 | 31.39 | 86.71 |
| 22 | 20 | 30 | 8 | 30 | 750 | 46.34 | 29.35 | 44.73 | 120.42 |
| 23 | 20 | 30 | 8 | 30 | 250 | 12.34 | 20.89 | 10.35 | 43.58 |
| 24 | 10 | 30 | 12 | 15 | 500 | 22.90 | 14.10 | 14.80 | 51.81 |
| 25 | 20 | 45 | 4 | 15 | 500 | 34.31 | 17.86 | 19.17 | 71.34 |
| 26 | 20 | 15 | 12 | 15 | 500 | 45.32 | 24.36 | 43.19 | 112.87 |
| 27 | 20 | 15 | 8 | 30 | 500 | 15.96 | 10.71 | 13.85 | 40.52 |
| 28 | 20 | 30 | 12 | 0 | 500 | 22.51 | 10.88 | 16.31 | 49.71 |
| 29 | 20 | 30 | 12 | 15 | 750 | 45.86 | 23.10 | 40.65 | 109.61 |
| 30 | 20 | 30 | 4 | 30 | 500 | 39.82 | 29.93 | 36.67 | 106.43 |
| 31 | 30 | 30 | 8 | 15 | 250 | 27.95 | 21.37 | 24.61 | 73.93 |
| 32 | 20 | 15 | 8 | 15 | 750 | 23.55 | 6.62 | 13.50 | 43.67 |
| 33 | 10 | 15 | 8 | 15 | 500 | 28.41 | 19.14 | 20.98 | 68.53 |
| 34 | 10 | 30 | 8 | 15 | 750 | 39.28 | 21.39 | 42.38 | 103.05 |
| 35 | 30 | 30 | 8 | 0 | 500 | 34.46 | 13.25 | 31.96 | 79.67 |
| 36 | 20 | 45 | 8 | 0 | 500 | 32.42 | 14.92 | 33.42 | 80.75 |
| 37 | 30 | 30 | 4 | 15 | 500 | 34.85 | 17.80 | 30.03 | 82.68 |
| 38 | 20 | 30 | 4 | 0 | 500 | 27.58 | 13.15 | 27.96 | 68.69 |
| 39 | 20 | 30 | 12 | 30 | 500 | 35.46 | 28.52 | 45.06 | 109.04 |
| 40 | 20 | 45 | 12 | 15 | 500 | 39.37 | 20.41 | 40.13 | 99.9 |
| 41 | 20 | 15 | 4 | 15 | 500 | 40.18 | 20.47 | 37.00 | 97.65 | n: number of trials

The data shown in Table 2 was subjected to multiple non-linear regression, and the experimental data for the enrichment factor of the NA compounds in the extractant solvent were fitted to the following equation, as described above, in order to develop quartic models capable of explaining the main and different degrees of interactive effects of the investigated parameters on the EFs, as well as predicting optimum extraction conditions. The nonlinear regression software also provided the analysis of variance (ANOVA) and estimated the coefficient parameters of the regression for the models. The quality of the developed quadratic models was further improved by dropping insignificant interaction effects that dwindled the respective response prediction accuracy. The reduced models in terms of coded factors are given below in equations (1), (2) and (3) for NDPA, NPIP and NDBA, respectively:

$$EF_{NDPA} = 33.96 + 2.29A + 2.04B + 2.30C - 1.41D + 8.14E + \\ 3.66AB + 3.29AC + 2.32AD - 0.020BC + 5.16BD + 4.52BE + \\ 0.18CD + 2.08CE + 11.49DE - 2.60A^2 + 4.58B^2 - 2.94C^2 + \\ 1.95D^2 + 2.35E^2 + 5.25A^2B - 1.62A^2C + 1.62AB^2 + \\ 4.36AC^2 + 0.25B^2C - 3.70B^2D - 5.73B^2E - 4.99BC^2 + \\ 1.08BD^2 + 7.70C^2D - 4.65CD^2 - 2.64D^2E - 7.51DE^2 + \\ 3.74A^2C^2 + 4.20B^2C^2 - 11.15B^2D^2 - 13.21B^2E^2 - 1.62C^2D^2 \quad (1)$$

$$EF_{NPIP} = 13.94 + 1.34A + 1.55B + 0.16C + 3.82D + 2.89E + 3.96AB + \\ 1.97AC + 1.46AD - 2.14AE - 0.34BC + 1.49BD + 2.57BE + \\ 0.21CD + 1.00CD + 1.41DE + 0.92A^2 + 3.48B^23.16C^2 + 2.79D^2 + \\ 3.45E^2 - 4.72B^2D - 5.68B^2E + 4.78C^2D - 5.91B^2D^2 - 5.45B^2E^2 \quad (2)$$

$$EF_{NDBA} = 29.02 + 5.40A + 1.01B + 2.22C - 5.50D + 12.29E + \\ 4.73AB + 5.69AC + 5.81AD - 0.097AE + 3.69BC + 2.19BD + \\ 6.44BE + 5.01CD + 1.46CE + 5.99DE + 0.15A^2 - 0.71B^2 + \\ 0.81C^2 + 0.77D^2 + 0.84E^2 - 7.64B^2E + 14.87C^2D - 11 \quad (3)$$

where EF is the enrichment factor, and NDPA, NPIP and NDBA are the NA compounds.

The coefficients of all variables of the quartic equations provided a measure of the effect of the level of the independent variables on the response ($EF_i$). In addition, positive and negative coefficients in the response functions indicate a synergistic and an antagonistic effect between the corresponding linear or interactive effect and the response, respectively. The qualities of the developed DLLME quadratic models were evaluated based on statistical test of hypothesis. As shown below in Table 3, the models' second-order regression coefficients ($R^2$) are 0.999, 0.877 and 0.833 for $EF_{NDBA}$, $EF_{NPIP}$ and $EF_{NDPA}$, respectively. The closer the $R^2$ value is to unity, the higher the model's accuracy in predicting the experimental values, thus indicating good prediction capabilities of the developed models. Further, all of the sources of variation of the three models' F-values, determined from ANOVA, indicated that the models are statistically significant at a 5% significance level (i.e., at probability values p<0.05). This further supports the fact that the three equations can adequately predict the experimental results with a high degree of accuracy. Similarly, the respective p-values established at either 5% or 10% significance levels (i.e., p<0.05 or p<0.1) suggest that all investigated parameters are significant model terms by considering the different sources of the model's variations, either as a single interaction (i.e., main effects as provided in Table 3), squared term, or higher interaction effects. Additionally, the adequate precision (measure of signal to noise ratio) for all the models shown below in Table 3 implies adequate signals (greater than 4 is desirable), thus indicating the models' suitability for navigating the design space for drawing credible conclusions.

TABLE 3

ANOVA for the Quartic Regression Model Obtained from Experimental Data

|  | $EF_{NDBA}$ ($R^2 = 0.999$) | | $EF_{NPIP}$ ($R^2 = 0.877$) | | $EF_{NDPA}$ ($R^2 = 0.833$) | |
| --- | --- | --- | --- | --- | --- | --- |
| Precision | 7.23 | | 8.59 | | 7.26 | |
|  | F-value | p-value | F-Value | p-value | F-Value | p-value |
| Model | 432.02 | 0.0023* | 4.3 | 0.0025* | 3.69 | 0.0039* |
| A | 209.59 | 0.0047* | 3.24 | 0.0922** | 8.67 | 0.0091* |
| B | 83.42 | 0.0118* | 4.35 | 0.0546** | 0.3 | 0.5886 |
| C | 105.91 | 0.0093* | 0.05 | 0.8288 | 1.46 | 0.2429 |
| D | 39.68 | 0.0243* | 13.19 | 0.0025* | 6.75 | 0.0188* |
| E | 2660.3 | 0.0004* | 11.33 | 0.0042* | 33.73 | 0.0001* |

*Significance was established at p < 0.05,
**Significance was established at p < 0.1

Considering the primary effects only, the coefficients of the independent variables were positive for NAs, except for the variable D in NDPA and NDBA, which were negative. This implies that a higher level of extraction time, volume of disperser solvent, pH and agitation speed are expected to result in a higher enrichment factor of NA compounds by using the DLLME technique. In this regard, the relative contributions of the main effects on the extraction of NAs from water could be ranked according to the order: agitation speed>extraction time>volume of disperser solvent>% of salt addition>pH.

Three-dimensional (3D) response surface curves and their corresponding contour maps for the EF quadratic models were constructed. This was to enable visualization and understanding of the influence of the independent variables and their relative interactions on the EFs. Each of the response curves was developed by fixing three of the independent variables while varying the remaining two within the investigated ranges. These curves corroborated the ANOVA analysis by revealing that all of the independent variables have significant contributions on the responses. They depicted the effect of all variables in the extraction of NAs, showing that the EFs of these three NA compounds were affected by all of the investigated variables (A-E).

The dependencies of the NA EFs on extraction time (A) and dispersive volume (B) at fixed values of initial pH of 12, 30% salt addition and 750 RPM agitation speed showed a trend of a linear increase in influence of extraction time on the extraction efficiencies of the NAs. This analysis resulted in an optimal extraction time of 25.77 minutes (see Table 4 below) for the three NAs tested. A trend of all EFs decreasing with an increase in dispersive volume was also seen. Thereafter, the extraction efficiency was seen to decrease continuously until the highest level of the dispersive volume was attained. As shown below in Table 4, an optimal average dispersive volume of 33.57 µL of methanol was determined by the analysis.

At fixed central values of initial pH of 12, 30% salt addition and a dispersive volume of 45 µL, the combined influence of agitation volume (E) and extraction time (A) further corroborated the linear effect of the influence of extraction time (A) on the extraction efficiencies for all of the NAs. A marked increase in the EFs with an increase in the agitation speed was seen, and exhibited exponential behavior for NDPA and NDBA. As shown below in Table 4, the optimal agitation speed for the three NAs was found to be 706.15 RPM. Overall, an increase in agitation speed and extraction time had a positive effect on the extraction efficiencies of the NAs using DLLME.

TABLE 4

Extraction Parameters for NAs

| NAs | Variables | | | | | EF | % RSD (n = 4) | Desirability |
| --- | --- | --- | --- | --- | --- | --- | --- | --- |
|  | A | B | C | D | E |  |  |  |
| NDPA | 27.25 | 35.30 | 10.51 | 20.46 | 723.07 | 52.81 | 0.27 | 1.00 |
| NPIP | 25.34 | 32.91 | 10.49 | 25.79 | 709.18 | 27.64 | 1.47 | 0.95 |
| NDBA | 24.80 | 32.62 | 10.44 | 16.60 | 684.48 | 44.20 | 2.66 | 0.89 |
| Average | 25.77 | 33.57 | 10.46 | 20.95 | 706.15 |  |  |  |

The response surface analysis further indicated that increasing salt concentration also showed exponential behavior for the respective EFs. This is because the solubility of the NAs in the aqueous phase was decreased with increasing salt concentration, reaching a maximum at 20.95% (w/v) salt concentration, as shown above in Table 4. While changing the pH level had a less significant effect overall, a stronger curvature was found for the NBDA extraction response surface. This may be due to hydrolysis of NBDA taking place for high alkaline pH.

The variability in the EF values from all tests clearly demonstrated that better EF values were more likely to be achieved for NDPA and NDBA, compared to NPIP. Thus, the analyses imply that among the three NAs investigated, NPIP is the least favorable for extraction in the water sample using DLLME. Further, the factors B, C, D and E are the main sources of the models' curvature, ranked in the order B>E>C>D. This means that the influence of these factors on EFs tend to deviate from linear, while that is not the case for factor A.

The optimum conditions for the extraction of NDBA, NDPA and NPIP, and the sum of these three NA compounds were predicted using coded values of the independent variables, with least parameters (i.e., 3 parameters) under investigation, finding the optimum region through visual inspection of the response surfaces (in the absence of constraints). However, for higher numbers of parameters, obtaining the global (rather than local) maximum point within the experimental variable ranges becomes more difficult. Thus, numerical optimization for simultaneous extraction of the NAs using DLLME was performed using Design-Expert® 8.0, a statistical software package manufactured by Stat-Ease®, Inc. of Minneapolis, Minn. The convergent criteria are composed of a set of goals based on desired constraints for the parameters of interest (i.e., responses and the independent variables). The criteria also weighted the individual parameters according to their relative importance in contributing towards attaining the desired overall targeted goals. The optimal numerical solutions for simultaneous extraction of the NAs that met the convergent criteria with highest desirability are shown in Table 4. The repeatability of forty-one (41) experimental runs for optimization of DLLME-GC/MS was calculated using the relative standard deviation of three trials for each run. RSD values between 0.44 and 11.4% were obtained in all cases.

To evaluate the semi-automated DLLME method, the linear range, repeatability and limits of detection (LODs) were investigated under the optimized condition. The results are summarized in Table 5 below.

TABLE 5

Semi-automated DLLME Method Validation

| | Linearity equation | $R^2$ | Linearity Range (L.R.) (μg/L) | % RSDs (n = 4) | LODs (3N/S) (ng/L) |
|---|---|---|---|---|---|
| NDPA | y = 0.0008x − 3.532 | 0.988 | 0.5-100 | 3.8 | 52 |
| NPIP | y = 0.0017x − 6.1137 | 0.997 | 0.1-100 | 5.9 | 32 |
| NDBA | y = 0.0009x − 2.3912 | 0.998 | 0.1-100 | 3.4 | 5.7 |

Very good linearity was observed over the concentration range of 0.1 to 100 μg/L for NAs, and with an excellent correlation of determination ($R^2$), ranging from 0.988 to 0.998. The repeatability study was carried out by extracting spiked water samples at differing concentration levels of 0.1, 0.5, 1.0, 10, 20, 37, 74 and 100 μg/L, and the percentage relative standard deviations (% RSDs) were between 3.4% and 5.9% (n=4). The LODs, based on a signal-to-noise ratio of S/N=3, ranged between 5.7 and 52 ng/L. Performance of semi-automated DLLME-SPME was compared with other conventional techniques, including solid phase extraction coupled with gas chromatography, electron ionization and mass spectrometry (SPE/GC-ET-MS-MS), headspace solid phase microextraction (HS-SPME/GC-MS-MS), high-performance liquid chromatography coupled with chemiluminescence detection (HPLC-CL), SPE coupled with a flame ionization detector (SPE/GC-FID), SPE coupled with a nitrogen phosphorous detector (SPE/GC-NPD), and SPE/GC-MS. These results are shown below in Table 6.

TABLE 6

Comparison of Semi-automated DLLME-GC/MS with Other Techniques for the Determination of NAs in Water Samples

| Method | Sample | L.R. (ng/L) | LODs (ng/L) | $R^2$ | % RSDs | % Recovery |
|---|---|---|---|---|---|---|
| SPE/GC-EI-MS-MS | Water | 500-50000 | 0.4-4 | 0.99 | max 10 | 82-102 |
| HS-SPME/GC-MS-MS | Water | 10-1500 | 1-5 | >0.995 | 3-13.0 | — |
| HPLC-CL | Water | 5-1000 | 1.5-3 | 0.999 | 0.7-4.5 | 94.8-102.8 |
| SPE/GC-FID | Water | 10000-600000 | 2000-3500 | >0.995 | 3-6.5 | — |
| SPE/GC-NPD | Water | 300-20000 | 20-80 | >0.995 | 3.5-6.3 | 95-103 |
| SPE/GC-MS | Water | 40-20000 | 3-13.0 | >0.995 | 4.1-6.1 | 95-103 |
| DLLME/GC-MS | Water | 100-100000 | 5.7-52 | >0.995 | 3.4-5.9 | 90.3-112 |

The results shown above in Table 6 clearly indicate that the performance of DLLME is more accurate than the other techniques in determination of NAs in water samples. The further advantages of the DLLME/GC-MS technique over the other methods include low limits of detection and high recoveries, as well as being within a good linear range.

In addition to prepared laboratory samples, the semi-automated DLLME/GC-MS method was applied to the determination of the N-nitrosamines NDPA, NPIP and NDBA in different types of water samples, including tap water, and groundwater samples (both before and after treatment) collected from a groundwater well and from a water purification plant on the main campus of King Fahd University of Petroleum and Minerals (KFUPM) in Dhahran, Saudi Arabia, respectively. Ten millimeters of each water sample were used for the DLLME extraction. Only NDBA was detected in the raw groundwater samples, as shown below in Table 7. NDPA and NPIP were not detected in other samples.

TABLE 7

Concentration (μg/L) of NAs in Real Water Samples

| | Groundwater at 25 m deep (n = 3) | | | | Tap (n = 3) | |
|---|---|---|---|---|---|---|
| NAs | Raw | % RSDs | After treatment | % RSDs | Water | % RSDs |
| NDPA | ND | 4.6 | ND | 7.9 | ND | 9.9 |
| NPIP | ND | 0.96 | ND | 12.3 | ND | 8.3 |
| NDBA | 0.8479 | 5.3 | ND | 1.7 | ND | 7.9 |

ND: Not determined

To assess the matrix effect of the DLLME-GC/MS method, the samples of Table 7 were spiked with 2 μg/L of target analytes and the extraction recoveries were calculated (shown below in Table 8). The recoveries for NAs in groundwater and tap water samples ranged from 90.3 to 112.1%. The sole drawing FIGURE shows the GC-MS total ion chromatograms of 10 mg/L of standard NAs in dichloromethane, fresh groundwater and fresh groundwater spiked by 2 μg/L of analytes.

TABLE 8

Extraction Recovery of NAs from Water Samples Spiked with NAs (2 μg/L)

| | Raw underground water | % RSDs (n = 3) | Treated underground water | % RSDs (n = 3) | Tap water | % RSDs (n = 3) |
|---|---|---|---|---|---|---|
| NDPA | 96.9 | 14.4 | 89.4 | 7.8 | 105.6 | 9.2 |
| NPIP | 91.9 | 6.9 | 92 | 13.6 | 94.2 | 7.3 |
| NDBA | 92.9 | 4.8 | 90.3 | 10.7 | 112.1 | 7.7 |

It is to be understood that the present invention is not limited to the embodiments described above, but encompasses any and all embodiments within the scope of the following claims.

We claim:

1. A dispersive liquid-liquid microextraction method of detecting N-nitrosoamines, comprising the steps of:
    adding microliters of an extraction solvent, the extraction solvent being xylene, and microliters of a disperser solvent, the disperser solvent being methanol, to microliters of an aqueous solution to form a test sample;
    agitating the test sample at an agitation speed of 706.15 RPM to form a cloudy suspension when an analyte is present in the test sample;
    allowing the test sample to separate into an organic phase and an aqueous phase;
    withdrawing an aliquot of the organic phase from the test sample with an extraction time of 25.77 minutes;
    directly injecting the aliquot into a gas chromatograph coupled with a mass spectrometer; and
    analyzing the aliquot by gas chromatography and mass spectrography for the presence of N-nitrosamines, wherein the steps of adding the microliters of the extraction solvent and the microliters of the disperser solvent, agitating the test sample, withdrawing the aliquot and directly injecting the aliquot are each performed by a programmable array logic auto-sampler.

2. The dispersive liquid-liquid microextraction method of detecting N-nitrosoamines as recited in claim 1, wherein the N-nitrosoamine is N-nitroso-di-n-propylamine, said step of analyzing the aliquot by gas chromatography further comprising the step of comparing the chromatogram of the aliquot with a chromatogram of a known standard sample of N-nitroso-di-n-propylamine.

3. The dispersive liquid-liquid microextraction method of detecting N-nitrosoamines as recited in claim 1, wherein the N-nitrosoamine is N-nitroso-di-n-butylamine, said step of analyzing the aliquot by gas chromatography further comprising the step of comparing the chromatogram of the aliquot with a chromatogram of a known standard sample of N-nitroso-di-n-butylamine.

4. The dispersive liquid-liquid microextraction method of detecting N-nitrosoamines as recited in claim 1, wherein the N-nitrosoamine is N-nitrosopiperidine, said step of analyzing the aliquot by gas chromatography further comprising the step of comparing the chromatogram of the aliquot with a chromatogram of a known, standard sample of N-nitrosopiperidine.

5. The dispersive liquid-liquid microextraction method of detecting N-nitrosoamines as recited in claim 1, further comprising the step of optimizing an extraction time for the withdrawal of the aliquot by response surface methodology and programming the programmable array logic auto-sampler with the optimized extraction time.

6. The dispersive liquid-liquid microextraction method of detecting N-nitrosoamines as recited in claim 5, further comprising the step of optimizing a volume of the disperser solvent by response surface methodology and programming the programmable array logic auto-sampler with the optimized volume of the disperser solvent.

7. The dispersive liquid-liquid microextraction method of detecting N-nitrosoamines as recited in claim 6, further comprising the step of optimizing an agitation speed for the agitation of the test sample by response surface methodology and programming the programmable array logic auto-sampler with the optimized agitation speed.

* * * * *